United States Patent [19]

Berger

[11] Patent Number: 6,090,799
[45] Date of Patent: Jul. 18, 2000

[54] METHOD FOR AMELIORATING MUSCLE WEAKNESS/WASTING IN A PATIENT INFECTED WITH HUMAN IMMUNODEFICIENCY VIRUS-TYPE 1

[75] Inventor: Joseph R. Berger, Miami, Fla.

[73] Assignee: BTG Pharmaceuticals Corp., Iselin, N.J.

[21] Appl. No.: 08/244,988

[22] PCT Filed: Oct. 20, 1993

[86] PCT No.: PCT/US93/10063

§ 371 Date: Jun. 22, 1995

§ 102(e) Date: Jun. 22, 1995

[87] PCT Pub. No.: WO94/08590

PCT Pub. Date: Apr. 28, 1994

[51] Int. Cl.[7] .................................................... A61K 31/56
[52] U.S. Cl. ............................................................ 514/179
[58] Field of Search ............................................... 514/179

[56] References Cited

FOREIGN PATENT DOCUMENTS 0222385   2/1993   European Pat. Off. .

OTHER PUBLICATIONS

O'Shea et al 74 CA: 75106a 1971.

Endo 73 CA: 95098g 1970.

*Primary Examiner*—Russell Travers
*Attorney, Agent, or Firm*—John P. White; Cooper & Dunham LLP

[57] ABSTRACT

A method for attenuating the HIV-associated myopathy and muscle wasting associated with infection by human immunodeficiency virus-Type 1. Administration of oxandrolone in a daily dosage of about 2.5 to about 20 milligrams is described.

8 Claims, No Drawings

METHOD FOR AMELIORATING MUSCLE WEAKNESS/WASTING IN A PATIENT INFECTED WITH HUMAN IMMUNODEFICIENCY VIRUS-TYPE 1

This application a 371 of PCT US 93/10063 Oct. 20, 1993.

TECHNICAL FIELD

The invention relates to the use of oxandrolone to attenuate myopathy and muscle weakness/wasting associated with infection by human immune deficiency virus-Type 1.

BACKGROUND OF THE INVENTION

Human immunodeficiency virus (HIV) associated myopathy and/or muscle weakness/wasting is a relatively common clinical manifestation of acquired immunodeficiency syndrome (AIDS). This is one of a number of neuromuscular disorders associated with the disease. There is some evidence to indicate that direct HIV infection of muscle may be at least partly responsible, occasionally resulting in a polymyositis-like disorder. In addition, zidovudine (AZT), an antiviral agent that is used widely in the clinical management of AIDS, has been associated with a toxic myopathy, presumably related to an inhibition of mitochondrial metabolism. In any event, the loss of muscle mass commonly observed in AIDS victims negatively impacts muscle function, however caused.

Individuals with HIV-associated myopathy or muscle weakness or wasting typically experience significant weight loss, generalized or proximal muscle weakness, tenderness, and muscle atrophy. Laboratory tests of samples from such individuals often reveal elevated levels of enzymes associated with muscle degeneration and necrosis, such as creatine kinase, aldolase, and aspartate amino transferase. Electromyographic test results for individuals with HIV-associated myopathy are typically consistent with myopathic changes. Histopathologic tests may reveal muscle fiber necrosis associated with lymphocytic inflammatory infiltrates. In AZT myotoxicity, ragged red fibers are often observed.

Clinical management of HIV-associated myopathy and muscle weakness/muscle wasting varies. In individuals with AZT myopathy, withdrawal of this anti-retroviral agent may be associated with temporary improvement in strength and muscle bulk. Corticosteroid therapy, such as the administration of prednisone, has been occasionally successful when inflammatory infiltrates have been detected in muscle. However, a potential drawback to this approach is that corticosteroids, because of their immunosuppressant activity, may be harmful to individuals with AIDS who are already dangerously immunosuppressed as a consequence of the HIV infection.

Furthermore, corticosteroid use itself is associated with myopathies and an increased susceptibility to infections. Plasmapheresis has also been used with some success, although at least one patient has experienced, despite an increase in muscle strength, substantial weakness over a period of several weeks.

SUMMARY OF THE INVENTION

The present invention provides a method which employs oxandrolone (an anabolic steroid with weak androgenic activity) as an alternative approach to the clinical management of HIV-associated myopathy/muscle weakness/muscle wasting. Loss in muscle mass (wasting) is attenuated, and body weight can be more readily maintained in this manner. Such an approach has been applied successfully to improve strength, reverse weight loss, and provide an improved sense of well-being.

Importantly, no evidence of liver injury or other untoward side effects have been observed.

Oxandrolone preferably is administered orally; however, other routes of administration can be utilized as well.

The present method of ameliorating muscle weakness or muscle wasting in a patient infected with HIV comprises administering to the patient daily a sufficient amount of oxandrolone to attenuate the patient's rate of muscle mass loss. To this end, oxandrolone may be administered, orally or otherwise, in a daily dose in the range of about 2.5 to about 20 milligrams. However, the response of individual patients may vary and in some instances a daily dose greater than 20 mg may be required to achieve the desired response. The daily dose may be divided into unit doses of about 1 to about 5 milligrams each, administered to the patient three times per day at about eight-hour intervals.

DETAILED DESCRIPTION OF THE PREFERRED EMBODIMENT

Oxandrolone (17-hydroxy-17-methyl-2-oxaandrostan-3-one) is a known compound that is commercially available. The preparation of oxandrolone is described, inter alia, in U.S. Pat. No. 3,128,283 to Pappo, which description is incorporated herein by reference.

Pharmacologically, oxandrolone is a synthetic anabolic steroid similar in structure to testosterone, but having a different, lesser androgenic/anabolic activity ratio. In addition, oxandrolone is unique among all other testosterone analogues in that it contains an oxygen atom instead of a methylene group at the 2-position of the phenanthrene nucleus. In addition, oxandrolone lacks a 4-ene function in its A-ring. The anabolic potency of oxandrolone, estimated as approximately 3 to 13 times that of testosterone, is believed to result form this unique structure.

Oxandrolone disposition and metabolism in man has been studied following oral administration of a 10 milligram dose. The study indicated that oxandrolone was rapidly and completely absorbed, yielding a mean peak plasma concentration of 417 micrograms of Oxandrolone per milliliter at 66 minutes. The plasma concentration of oxandrolone declined in a biphasic manner with a distribution half-life of approximately 30 minutes and an elimination half-life of 9.4 hours. Protein binding of oxandrolone was observed to be extensive.

In distinct contrast to other anabolic androgenic steroids such as methyltestosterone, fluoxymesterone, and micronized testosterone, oxandrolone taken orally is excreted mainly unchanged and unconjugated in urine. Urinary excretion of approximately 35 percent of an oral oxandrolone dose has been observed within 72 hours after ingestion. After 96 hours, approximately 65 percent of the administered oxandrolone dose was excreted in urine. Fecal excretion accounts for less than about 3 percent over the same time period.

Oxandrolone compositions, upon administration in accordance with this invention, ameliorate myopathy and muscle weakness in patients suffering from infections by human immunodeficiency virus-Type 1. Anabolic steroids, as a class, are known to stimulate appetite. Improved nutrition is important to individuals with AIDS who have experienced loss of lean body mass. Further, as a consequence of direct interaction with androgen and/or glucocorticoid receptors in muscle, anabolic steroids promote muscle anabolism through both anabolic pathways and anticatabolic pathways.

Anabolic steroids, such as oxandrolone, also increase protein synthesis. For example, oxandrolone increased muscle protein synthesis in a study of acute uremic rats. Similarly, administration of oxandrolone preceded clinical improvement in appetite, cell mass, human growth, and weight for height in boys with chronic renal failure. These observations are consistent with anabolic activity. Oxandrolone may also stimulate the secretion of growth hormone and insulin-like growth factors.

In addition to producing beneficial direct anabolic action, oxandrolone is also believed to act as a delayed immunostimulant. In contrast, other appetite stimulants, such as dronabinol, that are currently under evaluation as appetite stimulants for AIDS patients can act as immunosuppressants in animals.

For purposes of administration in accordance with this invention, the active ingredient oxandrolone is combined with solid or liquid pharmaceutical carriers and formulated in unit dosage form using pharmacologically acceptable excipients, or dissolved or suspended in physiologically acceptable solvents or liquid vehicles for oral, percutaneous, or topical administration.

The overall daily dose of oxandrolone to provide a therapeutically effective amount in accordance with the method of this invention can be as low as about 2.5 milligrams and as high as about 20 milligrams, depending upon the patient's response and the mode of administration.

The amount of the active ingredient within the aforementioned ranges that is to be administered depends upon the age, weight and condition of the patient, as well as on factors such as the frequency and route of administration. In formulating oxandrolone, it is recognized that there may be differences between the immediate and the long term response. To account for these changes, the specific dosage given to a particular patient is based also on the individual patient's response. Preferably, oxandrolone is orally administered to the patient daily for a time period in the range of about 2 weeks to about 6 months.

Attenuation of the rate of muscle mass loss in a patient can be ascertained by comparing the patient's rate of weight loss before oxandrolone therapy with that after the administration of oxandrolone has been commenced. Alternatively, or in addition, the patient's urinary nitrogen level can be monitored, a well-known expedient. A decrease in the patient's urinary nitrogen level is indicative of a decrease in muscle mass loss.

Similarly, the maintenance of a relatively stable patient's total body potassium level, as well as an increase in the patient's total body potassium level, upon oxandrolone administration indicates that a therapeutically effective amount of oxandrolone is being administered. A patient's total body potassium level can be monitored, for example, as described in Kotler et al., The American Journal of Clinical Nutrition, 42:1255–1265 (December 1985) and Pierson, Jr., et al., Am. J. Physiol., 246 (Renal Fluid Electrolyte Physiol. 15) :F234–F239 (1984).

The route of administration can be oral, percutaneous, transdermal, sublingual, buccal, intravenous, intramuscular, or the like. Of these, oral administration is preferred. The patient's daily dose of the active ingredient preferably is in the range of about 7.5 milligrams, but may exceed 20 milligrams based on clinical response. This daily dose can be given in tablet form as a single dose, or as plural divided doses, preferably 2 to 3 divided doses. The requisite daily dose can also be supplied continuously, for example, by a transdermal patch worn by the patient or intravenously. If the oxandrolone is administered orally, dosages in the range of about 2 to about 5 milligrams three to four times daily typically may be prescribed.

Oxandrolone tablets are manufactured using standard solid dose form technology in accordance with United States Pharmacopeia (USP) specifications (see, for example, The United States Pharmacopeia, 22nd Revision, pp. 981–982). Specifically, a typical 150-milligram tablet contains the following:

| | |
|---|---|
| Oxandrolone, USP | 2.5 mg |
| Corn Starch, NF | 30.0 mg |
| Lactose NF (hydrous) | 113.0 mg |
| Hydroxypropyl Methylcellulose, USP | 3.0 mg |
| Magnesium Stearate | 1.5 mg |
| | 150.0 mg |

The terms "unit dosage form" and "unit dose" as used in the present specification and claims refer to a physically discrete unit or units suitable as unitary doses for patients, each unit containing a predetermined quantity of the active ingredient calculated to produce the desired therapeutic effect in association with the pharmacologically acceptable carrier. The specifications for the unit dosage forms of this invention are dictated in part and are also dependent upon (a) the unique characteristics of the active ingredient and (b) the particular therapeutic effect to be achieved, as well as upon limitations inherent in the art of compounding such active ingredient for the therapeutic use disclosed in detail in this specification. Examples of suitable unit dosage forms in accordance with this invention are tablets, pills, powder packets, wafers, cachets, segregated multiples of any of the foregoing, transdermal patches, aliquots of injectables, and the like forms.

The primary response variables are patient's total body potassium, body weight, muscle mass, muscle strength, improvement in or increased appetite, and general sense of well-being. In addition, improvement in immune status (or at a minimum, no worsening of immune function) in response to oxandrolone is significant as well.

An important question regarding the use of any drug in combination with anti-retroviral therapy is whether drug interactions may occur that would diminish AZT efficacy or increase the frequency of severity of AZT-related adverse reactions. TABLE 1 compares various published pharmacological parameters for oxandrolone and AZT and illustrates important differences between the two drugs.

TABLE 1

Comparison of Selected Oxandrolone and AZT Pharmacology Parameters

| Parameter | Oxandrolone | AZT |
|---|---|---|
| Oral Bioavailability | 100% | 65% |
| Tmax | 1.1 hr | 0.7 hr |
| Biological T1/2 | 9.4 hr | 1.1 hr |
| Vd | 578 ml/kg | >1400 ml/kg |
| Protein Binding | >95% | 25–35% |
| Plasma Clearance | 43 ml/kg/hr | >1300 ml/kg/hr |
| Metabolism | Little | Extensive |

TABLE 1-continued

Comparison of Selected Oxandrolone
and AZT Pharmacology Parameters

| Parameter | Oxandrolone | AZT |
|---|---|---|
| Glucuronidation | Little | Substantial |
| Urinary Excretion | Extensive; primarily parent compound | Extensive; parent and glucuronide conjugated |
| Target Organ Toxicity | Liver (anabolic steroids as a class) | Hematopoietic system (e.g., anemia, granulocytopenia) |
| Known Drug Interactions | Anticoagulants; oral hypoglycemic agents; adrenal steroid when edema present | Drugs that may: (a) inhibit glucuronidation (e.g., aspirin, acetaminophen) or urinary excretion (e.g., probenecid); (b) adversely affect blood cell number and function; and (c) nephrotoxic or cytotoxic |

Because oxandrolone is primarily protein bound, whereas AZT is primarily non-protein bound, oxandrolone will not compete appreciably with AZT for binding sites in plasma. Consequently, administration of oxandrolone to patients on AZT therapy is unlikely to alter the level of free AZT in the blood. Likewise, the administration of AZT is unlikely to alter the level of free oxandrolone in the blood. An oxandrolone-AZT drug interaction involving binding site displacement is, therefore, extremely unlikely.

AZT is rapidly metabolized and excreted in the urine—a significant quantity is excreted in the form of glucuronide conjugates. In sharp contrast, oxandrolone, perhaps due to presence of a lactone group and the absence of a 4-ene function in the A-ring, undergoes little hepatic metabolism and is excreted primarily unchanged and unconjugated in urine. Thus, in contradistinction to other drugs that may competitively inhibit glucuronidation and thereby potentially slow the rate of AZT metabolism, such as aspirin, acetaminophen, or indomethacin, the present active agent, oxandrolone, is not believed to affect AZT metabolism.

Furthermore, oxandrolone is neither nephrotoxic nor cytotoxic. Accordingly, oxandrolone is not expected to interfere with the renal excretion of AZT or its metabolites. To the contrary, oxandrolone has been safely and effectively used in patients with chronic renal disease to stimulate growth and increase lean body mass. In well-controlled studies of oxandrolone for the clinical management of critically ill patients with acute alcoholic hepatitis, oxandrolone administered at daily doses of up to 80 mg/day for four weeks and 40 mg/day for eight weeks did not result in any drug-related nephrotoxicity.

While it is known that anabolic androgenic steroids have been associated with potentially life-threatening forms of liver disease, including peliosis hepatis, cholestatic jaundice, and hepatocellular neoplasms, specific reports in the medical literature regarding liver disease in oxandrolone-treated patients, at the dosages proposed for use in the clinical management of HIV associated muscle weakness/wasting (i.e., about 2.5 to about 20 mg/day) are rare.

Oxandrolone and AZT have different mechanisms of action. They also function in different sites of cellular action at the receptor level. Oxandrolone functions via interaction with androgen and glucocorticoid receptors, whereas AZT, once phosphorylated, acts to inhibit HIV reverse transcription. Thus, competitive inhibition of AZT by oxandrolone at the cellular level also is considered unlikely.

Neither has oxandrolone been associated with anemia or granulocytopenia, two frequently occurring and potentially serious side effects associated with AZT therapy. To the contrary, anabolic androgenic steroids have been used clinically to stimulate ethyropoiesis in hypoanemias, aplastic anemias, hemolytic anemias, renal anemias, anemias due to cytotoxic therapy, and various leukemias. It has been reported recently that androgens augment beneficial effects of erythropoietin in the treatment of anemia resulting from end-stage renal disease.

Data derived from animal models and human clinical studies indicate that anabolic steroids are unlikely to suppress immune function in patients infected with HIV. For example, anabolic steroids can stimulate granulopoiesis in mice, as evidenced by stimulation of granulocytic colony-forming cells derived from spleen and bone marrow. Similarly, an anabolic steroid known as nandrolone decanonate enhanced macrophage activity and cell-mediated immunity in patients with uterine cervical cancer when administered parentally. In related studies, anabolic steroids increased peripheral lymphocyte and monocyte counts, Immunoglobin G (IgG) levels, and PHA-blastoid transfromation of peripheral lymphocytes. In those studies, $\beta_2$-microglobulin levels simultaneously decreased.

IgG is one of a class of antibodies secreted by B cells (i.e., B-lymphocytes) in response to an antigenic challenge (e.g., foreign protein like that from bacteria). In the case of HIV infection, humoral immune function (i.e., B-cell mediated) is significantly impaired. Accordingly, when HIV-infected individuals are challenged with a specific antigen, the typical response of B-cell proliferation, differentiation and secretion of antibodies (e.g., IgG) is diminished or absent. This decline in humoral immune function coupled with defects in cellular immune (i.e., T-cell) function contributes to the overall failure of the immune system to respond in an appropriate manner to challenge. B-cells in AIDS victims are, by mechanisms unknown, hyperstimulated to secrete large amounts of immunoglobulins that make the humoral system refractory to new antigens. The result is that the patient's system no longer recognizes new antigens and does not respond.

In animal studies in which anabolic steroids have been reported to increase IgG and PHA-blastoid activity, these changes occurred as a result of immune system stimulation, and are positive responses. β-microglobin is a cell surface protein that is found on all nucleated calls and it is released into the serum during cell turnover. Generally, β-microglobulin is considered a marker of infectious, inflammatory, malignant and autoimmune disease activity. In several AIDS studies, β-microglobulin levels correlated with disease progression and T4 (T-helper) cell counts. In the case of therapy with oxandrolone, for example, a decrease in β-microglobulin levels is desirable. Thus, animal data showing reduced plasma levels of β-microglobulin in response to anabolic steroids is evidence of a positive effect and suggestive of similar activity in man.

Accordingly, there are no reasons to believe that the administration of an anabolic steroid in general and oxandrolone in particular would have adverse effects on the immune system. Generally, the target organ of toxicity for these drugs is the liver—probably because this is where most are metabolized. Oxandrolone, however, has a remarkably good safety profile in man as a likely consequence of its resistance to hepatic metabolism; an oral dose is excreted primarily in urine as the parent compound, as stated hereinabove.

Data from clinical trials in patients with severe alcoholic liver disease provide further evidence that oxandrolone is not likely to suppress immune function in patients with HIV infection. Ethanol abuse is associated with loss of lymphocyte functions, particularly T-cell dependent immune responses. Previous researchers have observed that oxandrolone significantly improved lymphocyte number in patients with severe alcoholic hepatitis. Because the loss of lymphocytic function by alcoholic liver disease parallels, to a significant degree, the loss of T-cell function due to HIV infection, it is reasonable to hypothesize that oxandrolone will increase the T-Cell function of HIV-infected patients.

Therefore, these data from laboratory animals and human studies indicate that suppression of the immune system by anabolic steroids, such as oxandrolone, is unlikely. Nonetheless, subjects undergoing oxandrolone therapy, as a precaution, should be monitored for changes in lymphocyte number, particularly CD4+ and CD8+, as is routinely done for patients who undergo steroid therapy.

In summary, based on the differences between AZT and oxandrolone with respect to pharmacokinetics, metabolism, reported drug interactions, mechanisms of action, and reported toxicities, oxandrolone and AZT can be safely used in combination for subjects infected with the Type-1 HIV virus and suffering from HIV-associated myopathy. The use of oxandrolone in patients on AZT therapy is, on the basis of known drug interactions, also consistent with current FDA-approved labeling for AZT and oxandrolone.

The following example demonstrates the effectiveness of oxandrolone in attenuating the effects of HIV-associated muscle weakness or muscle wasting in an AIDS patient.

EXAMPLE

A patient, a thirty-two year old homosexual man, known to be HIV-seropositive since February 1989, noted difficulty opening drawers and bottles in May 1989. The patient weakened progressively and, during a physical examination in September 1989, demonstrated by confrontation testing the weakness of neck flexion and proximal limbs. However, his muscle stretch reflexes remained normal. Laboratory tests showed the patient's creatine kinase level to be 286 International Units per liter, much higher than the normally observed range for creatine kinase of about 40–200 Units per liter.

Zidovudine (azidothymidine or AZT) was initiated at 500 milligrams daily, but the patient's strength continued to decline through February 1990. He complained of an inability to ascend a flight of stairs. The patient exhibited greater weakness and atrophy of neck flexors and extremity muscles during another physical examination performed at this time. An electromyogram revealed a decrease of amplitude and duration of the patient's motor unit potentials and increased recruitment in selected muscles of his right upper extremity. The patient's creatine kinase tested at 456 Units per liter. A muscle biopsy revealed numerous myofibers, abundant ragged red fibers, and numerous eosinophilic inclusions. Round cell inflammatory infiltrates were also noted. In light of these developments, the zidovudine treatment was terminated.

Substantial improvement initially followed the discontinuation of zidovudine. However, because of a subsequent continued and progressive weakness rendering it difficult for the patient to ascend or descend a flight of stairs, a prednisone therapy (60 mg daily) was initiated. No significant improvement accompanied the use of prednisone.

Thereafter, a trial period of oral oxandrolone administration (2.5 milligrams, three times daily, in tablet form) was initiated. Within two weeks of the initiation of the oxandrolone therapy, the patient noted an improved sense of well being, became stronger, and gained weight. Within one month, he was able to ascend and descend stairs without problems. Confrontation testing revealed nearly normal strength. The patient's weight increased from 115 pounds to 130 pounds. The patient's muscle atrophy was alleviated as well. Liver functions were closely monitored for signs of elevation, but undesirable side effects were not detected.

After several months of the aforementioned therapy with oxandrolone, the patient was no longer able to obtain oxandrolone for use as a medication. Weakness and weight loss ensued. Trials of other anabolic preparations, specifically stanazol and oxymethalone, did not return the patient to his previous levels of function and strength.

The EXAMPLE demonstrates that oxandrolone can be a beneficial alternative for clinical management of HIV-associated myopathy and muscle weakness and wasting.

It is intended that the foregoing description is by way of illustration only and is not to be construed as limiting the invention in any way except in the spirit and scope of the appended claims.

What is claimed is:

1. A method for ameliorating HIV-associated myopathy and muscle weakness in an AIDS patient which comprises orally administering oxandrolone to the AIDS patient in a daily dosage of between about 2.5 to about 7.5 milligrams.

2. The method in accordance with claim 1 wherein the daily dosage of the oxandrolone is about 7.5 milligrams.

3. The method in accordance with claim 1 wherein the oxandrolone is administered to said patient as a unit dose of about 1 to about 2.5 milligrams three times per day at about eight-hour intervals.

4. The method in accordance with claim 1 wherein the oxandrolone is administered in the form of a tablet.

5. The method in accordance with claim 1 wherein administration is continued over a period of about 2 weeks.

6. The method in accordance with claim 1 wherein administration is continued over a period of about 2 weeks.

7. The method in accordance with claim 3 wherein administration is continued over a period of about 2 weeks.

8. A method for ameliorating HIV-associated myopathy and muscle wasting in an AIDS patient which comprises orally administering a therapeutically effective amount of oxandrolone to the AIDS patient daily for a time period of about 2 weeks.

\* \* \* \* \*

UNITED STATES PATENT AND TRADEMARK OFFICE
CERTIFICATE OF CORRECTION

PATENT NO. : 6,090,799
DATED : Jul. 18, 2000
INVENTOR(S) : Joseph R. Berger

It is certified that error appears in the above-identified patent and that said Letters Patent is hereby corrected as shown below:

On title page, item [73] should read --Bio-Technology General Corp.--

Signed and Sealed this

Thirty-first Day of October, 2000

Attest:

Q. TODD DICKINSON

*Attesting Officer*         *Director of Patents and Trademarks*